United States Patent [19]

Mervine

[11] Patent Number: 4,955,879
[45] Date of Patent: Sep. 11, 1990

[54] URINARY DRAINAGE DEVICE

[75] Inventor: Jeanne A. Mervine, Chicago, Ill.

[73] Assignee: Rehabilitation Institute of Chicago, Chicago, Ill.

[21] Appl. No.: 281,909

[22] Filed: Dec. 7, 1988

Related U.S. Application Data

[63] Continuation-in-part of Ser. No. 28,350, Mar. 20, 1987, abandoned.

[51] Int. Cl.⁵ ............................................. A61M 1/00
[52] U.S. Cl. ...................................... 604/327; 604/317
[58] Field of Search ............................... 604/322–327, 604/331, 345, 349–353, 410; 128/760–762, 767

[56] References Cited

U.S. PATENT DOCUMENTS

| | | | |
|---|---|---|---|
| 3,231,901 | 2/1966 | Kennedy | 604/322 |
| 3,554,256 | 1/1971 | Anderson | 604/408 |
| 3,601,119 | 8/1971 | Engelsher | 604/325 |
| 3,613,123 | 10/1971 | Langstrom | 4/144.1 |
| 3,897,785 | 8/1875 | Barto, Jr. | 604/345 |
| 3,943,929 | 3/1976 | Patel | 604/324 |
| 4,000,649 | 1/1977 | Hanifl | 128/762 |
| 4,391,138 | 7/1983 | Harle | 604/322 |
| 4,421,509 | 12/1983 | Schneider et al. | 604/327 |
| 4,462,510 | 7/1984 | Steer et al. | 604/323 |

FOREIGN PATENT DOCUMENTS

| | | | |
|---|---|---|---|
| 0677593 | 1/1964 | Canada | 604/322 |
| 3319929 | 12/1983 | Fed. Rep. of Germany | 604/327 |

Primary Examiner—J. L. Kruter
Attorney, Agent, or Firm—Kirkland & Ellis

[57] ABSTRACT

A urinary drainage device that can be used as both a nighttime drainage container and a daytime, ambulatory drainage device. The device is flexible and can be folded and strapped to a patient's leg for ambulatory use or hung on the side of a patient's bed for stationary use.

4 Claims, 1 Drawing Sheet

URINARY DRAINAGE DEVICE

This is a continuation-in-part of co-pending application Ser. No. 07/028,350 filed on Mar. 20, 1987 now abandoned.

BACKGROUND OF THE INVENTION

The present invention relates to urinary drainage devices and more particularly to urine receptacles for patients with internal or external catheters. Although urinary receptacles of this type are presently known the invention described herein is unique because it permits both nighttime stationary use, and daytime, ambulatory use.

SUMMARY OF THE INVENTION

A principal feature of the present invention is the provision of a flexible urinary drainage device that has the volume capacity to be used as a night drainage device that can be folded and attached to the leg using straps for daytime ambulatory use.

The urinary drainage device of the present invention comprises a flexible container made of plastic or other suitable material having a plurality of flexible chambers to receive urine, with means for connecting a catheter tube to one of the chambers of the container and other means for draining urine from the container. The container is sufficiently flexible so as to be foldable along a line separating the chambers into which the urine flows from the catheter tube.

When the urinary drainage device of the present invention is unfolded and hung on the side of the bed, it can be used as a night drainage device so that urine flows into each of the chambers in the container. When unfolded the device has sufficient volume to be used without being drained during the night.

When the urinary drainage device of the present invention is folded along the lines separating the chambers, it can be attached to a patient's leg using straps. The patient using the device will therefore have increased mobility and be able to walk or move around without changing to another urinary drainage device.

Another feature of the present invention is the decrease in the chances of the patient contracting urinary infection because the urinary drainage device used by the patient would not have to be changed every morning from a nighttime, stationary device to a daytime, ambulatory device.

Another feature of the invention is the decrease in the amount of skilled nursing care and time allowed for changing of urinary drainage deVices.

Further features will become more fully apparent in the following description of the preferred embodiment of this invention and from the appended claims.

DESCRIPTION OF THE PREFERRED EMBODIMENT

Figure 1:
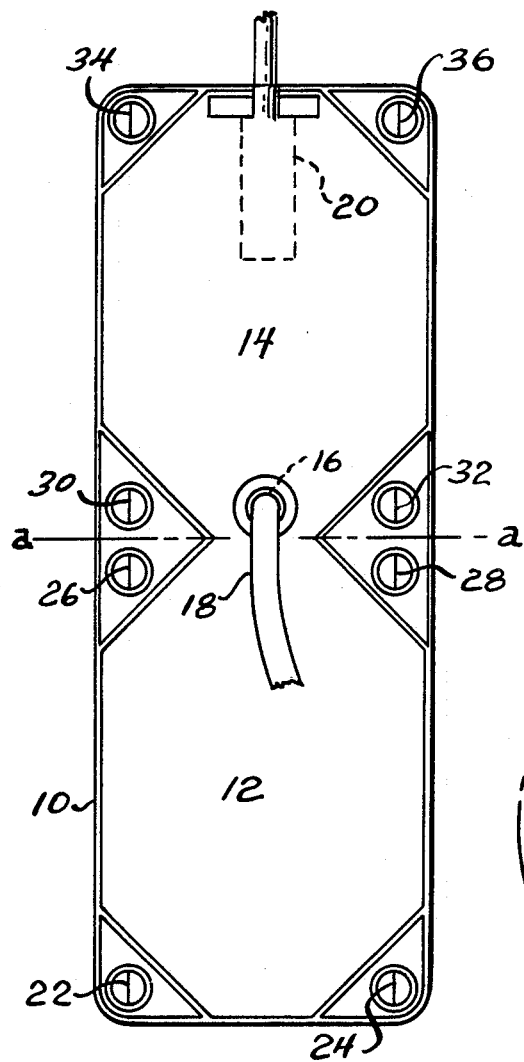
FIG. 1 is a top view of the urinary drainage device when it is unfolded.

Referring now to FIG. 1, there is shown a urinary drainage device 10 having two chambers 12 and 14. The walls of chambers 12 and 14 are made of flexible material so that it will lie flat when the urinary drainage device 10 is empty but will expand when urinary drainage device 10 becomes filled.

Urinary drainage device 10 has a one-way valve 20 into which is inserted a catheter. Urinary drainage device 10 also has a drainage valve 16, which is used to drain the device when it becomes full. Tube 18 is connected to drainage valve 16 to allow easier drainage.

Figure 2:
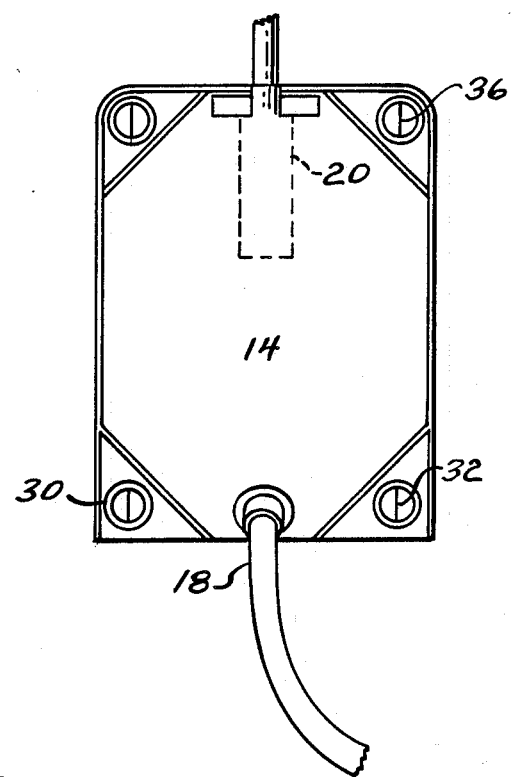
FIG. 2 is a top view of the urinary drainage device when it is folded.
Figure 3:
FIG. 3 is a side view of the urinary drainage device when it is folded.

Urinary drainage device 10 also has eight strap holders 22, 24, 26, 28, 30, 32, 34 and 36, into which flexible straps may be inserted when the device is folded. Referring particularly to FIG. 1, urinary drainage device 10 is foldable along line a—a on the device, which forms an indicia for folding. Referring more particularly to FIGS. 1, 2, and 3, urinary drainage device 10 may be folded along line a—a so that valve 20 protrudes only into chamber 14. One way valve 20 drains only into chamber 14 when urinary drainage device 10 is folded.

Figure 4:
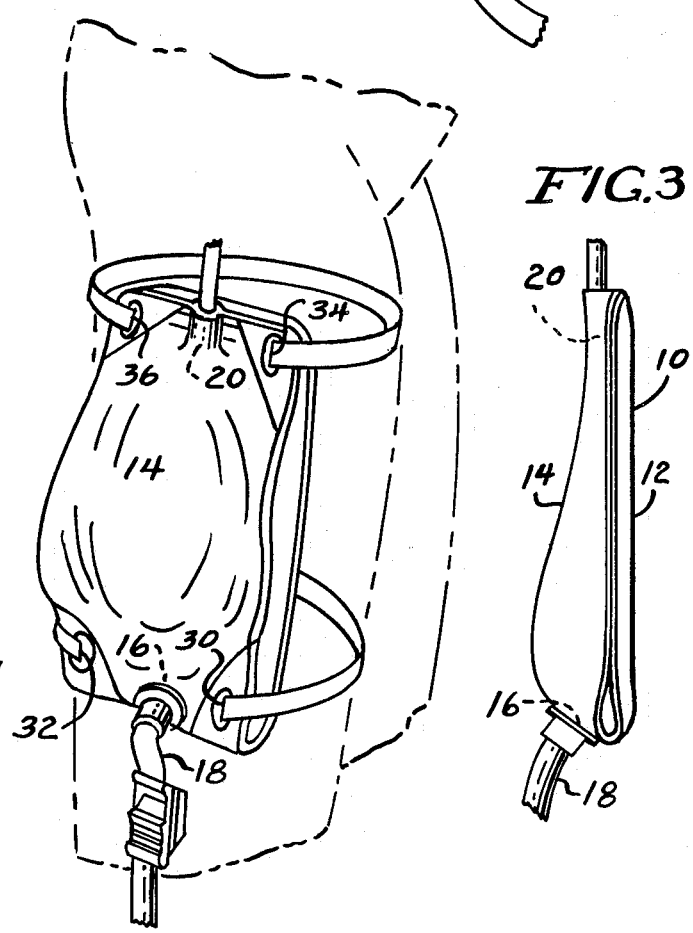
FIG. 4 is a side elevational view showing the folded urinary device as it would be strapped to a patient's leg.

Referring to FIG. 4, urinary drainage device 10 may be folded along lines a—a and strapped longitudinally to a patient's leg by inserting flexible strap 38 through strap holders 22, 34, 36 and 24, then wrapping flexible strap 38 around the upper part of the patient's leg near the crotch. In addition, urinary drainage device 10 may be more securely fastened to the lower part of the patient's thigh by inserting flexible strap 40 through strap holder 22, 34, 36 and 24, then wrapping flexible strap 40 around the lower part of the patient's thigh.

Although a preferred embodiment of the invention has been illustrated and described, various modifications and changes may be resorted to without departing from the spirit of the invention or the scope of the appended claims, and each of such modifications and change is contemplated.

What is claimed is:

1. A urinary drainage device adapted for wear by male or female patients with indwelling or external catheters, said device comprising:
    a flexible container having a first end and a second end connected along a transverse line, said container being foldable along said transverse line into a pair of chambers of substantially equal size along said transverse line;
    means for connecting said container to an indwelling or external catheter, said means being connected to said first end on said container, said means being fluidwise connected to only one of said chambers when said container is folded along said transverse line; and
    means for draining said container, said means being fluidwise connected to only the same chamber as the means for connecting when said container is folded along said transverse line, wherein when folded and in use the first and second ends and the means for connecting are at an uppermost position and the means for draining is at a lowermost position.

2. A urinary drainage device as described in claim 1, wherein said container has a plurality of slots or strap holders.

3. A urinary drainage device as described in claim 1, wherein said container has a flexible strap connected to it.

4. A urinary drainage device as described in claim 1, wherein said container has a plurality of hooks connected to it.

* * * * *